United States Patent
Sugimoto

(10) Patent No.: US 10,093,599 B2
(45) Date of Patent: *Oct. 9, 2018

(54) METHOD FOR MANUFACTURING FLUORINATED HYDROCARBON

(71) Applicant: ZEON CORPORATION, Chiyoda-ku, Tokyo (JP)

(72) Inventor: Tatsuya Sugimoto, Tokyo (JP)

(73) Assignee: ZEON CORPORATION, Chiyoda-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/747,752

(22) PCT Filed: Jul. 26, 2016

(86) PCT No.: PCT/JP2016/071881
§ 371 (c)(1),
(2) Date: Jan. 25, 2018

(87) PCT Pub. No.: WO2017/022571
PCT Pub. Date: Feb. 9, 2017

(65) Prior Publication Data
US 2018/0215688 A1    Aug. 2, 2018

(30) Foreign Application Priority Data

Aug. 5, 2015   (JP) .................. 2015-155197

(51) Int. Cl.
C07C 17/093   (2006.01)
C07C 19/08    (2006.01)

(52) U.S. Cl.
CPC ............ *C07C 17/093* (2013.01); *C07C 19/08* (2013.01); *C07C 2521/04* (2013.01); *C07C 2521/06* (2013.01); *C07C 2527/1213* (2013.01)

(58) Field of Classification Search
CPC ... C07C 17/361; C07C 31/146; B01J 2231/42
See application file for complete search history.

(56) References Cited

U.S. PATENT DOCUMENTS

| | | | |
|---|---|---|---|
| 2,550,953 | A | 5/1951 | Barrick |
| 4,407,731 | A | 10/1983 | Imai |
| 2011/0068086 | A1 | 3/2011 | Suzuki et al. |
| 2017/0174588 | A1 | 6/2017 | Sugimoto |

FOREIGN PATENT DOCUMENTS

| | | | |
|---|---|---|---|
| JP | S5946251 A | | 3/1984 |
| JP | 2009292749 A | | 12/2009 |
| WO | WO 00113792 | * | 3/2000 |
| WO | 2009123038 A1 | | 10/2009 |
| WO | 2015122386 A1 | | 8/2015 |

OTHER PUBLICATIONS

Chikai Kimura et al., "Alkylation of Butyl Alcohols by Dialkyl Sulfates Using Phase Transfer Catalysis", Journal of Japan Oil Chemists' Society, 1982, pp. 960-962, vol. 31, No. 11.
James F. Norris et al., "The Reactivity of Atoms and Groups in Organic Compounds. XII. The Preparation and Properties of Mixed Aliphatic Ethers With Special Reference to Those Containing the Tert.-Butyl Radical", Journal of the American Chemical Society, May 1932, pp. 2088-2100, vol. 54.
James H. Clark et al., "Reactions of Potassium Fluoride in Glacial Acetic Acid with Chlorocarboxylic Acids, Amides, and Chlorides. The Effect of Very Strong Hydrogen Bonding on the Nucleophilicity of the Fluoride Anion", Journal of the Chemical Society, Dalton Transactions, 1975, pp. 2129-2134.
Michael B. McGinnis et al., "Selectivities of Diels-Alder Reactions Catalyzed by Highly Acidic Boronated Aluminas", The Journal of Organic Chemistry, 1996, pp. 3496-3500, vol. 61, No. 10.
N. O. Calloway, "Reactions in the Presence of Metallic Halides. II. The Behavior of Fluorides and the Reactivity of the Halogens", Journal of the American Chemical Society, Aug. 1937, pp. 1474-1479, vol. 59.
Zennosuke Suzuki et al., "An Acid-catalyzed Reaction of Methyl Ethers with Acetyl Fluoride. Syntheses of 1-Fluorobicyclo[2.2.2]octanes", Bulletin of the Chemical Society of Japan, Jul. 1968, pp. 1724-1725, vol. 41, No. 7.

* cited by examiner

*Primary Examiner* — Jafar F Parsa
(74) *Attorney, Agent, or Firm* — Kenja IP Law PC

(57) ABSTRACT

The present invention is a method for producing a fluorinated hydrocarbon represented by a structural formula (3), wherein an ether compound represented by a structural formula (1) and an acid fluoride represented by a structural formula (2) are brought into contact with each other in a hydrocarbon-based solvent, in the presence of a catalyst in which boron trifluoride is supported on a metal oxide: wherein $R^1$ and $R^2$ represent an alkyl group having 1 to 3 carbon atoms, $R^3$ represents a hydrogen atom, a methyl group or an ethyl group, and $R^4$ and $R^5$ represent a methyl group or an ethyl group; and $R^1$ and $R^2$ may be bonded to each other to form a cyclic structure. Through the present invention, a method for industrially advantageously producing 2-fluorobutane is provided.

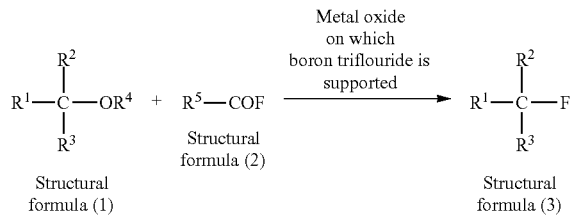

5 Claims, No Drawings

METHOD FOR MANUFACTURING FLUORINATED HYDROCARBON

TECHNICAL FIELD

The present invention relates to a method for producing fluorinated hydrocarbons useful as plasma reaction gases in plasma etching, plasma chemical vapor deposition (plasma CVD) and the like effective in the field of producing semiconductor devices, useful as fluorine-containing medical intermediates, and useful as hydrofluorocarbon-based solvents. Highly purified fluorinated hydrocarbons are suitable as plasma etching gases, plasma CVD gases and the like, in particular, in the field of producing semiconductor devices using plasma reaction.

BACKGROUND ART

Recently, miniaturization of semiconductor production techniques has increasingly progressed, in such a way that the state-of-the-art process has adopted generations having wiring widths of the order of 20 nm and further 10 nm. Miniaturization goes with the enhancement of the technical difficulty in the miniaturization processing, and technical developments have been progressed from various aspects of approach, with respect to the materials, apparatuses, processing methods and others to be used.

Under such circumstances, the present applicant has also developed a dry etching gas capable of coping with the state-of-the-art dry etching process, and has discovered that saturated fluorinated hydrocarbons having small number of fluorine atoms such as 2-fluorobutane have performances surpassing monofluoromethane being used in etching of silicon nitride films (Patent Literature 1).

Several methods for producing 2-fluorobutane have hitherto been known. For example, Patent Literature 2 describes a production of 2-fluorobutane in a yield of 46%, by bringing N,N'-diethyl-3-oxo-methyltrifluoropropylamine as a fluorinating agent into contact with 2-butanol. Patent Literature 3 discloses that the production of fluorinated sec-butyl was confirmed by bringing sulfur hexafluoride into contact with a sec-butyllithium solution in a cyclohexane/n-hexane mixed solvent. Patent Literature 4 describes the preparation of 2-fluorobutane by hydrogenation of 2-fluorobutadiene in the presence of a catalyst. Non Patent Literature 1 also discloses a method for preparing monofluorinated hydrocarbons by acting acetyl fluoride as a fluorinating agent to ether compounds having a cyclic structure such as adamantyl methyl ether and cyclohexyl methyl ether in the presence of a catalyst such as boron trifluoride phosphoric acid complex or zinc fluoride.

CITATION LIST

Patent Literature

Patent Literature 1: WO2009-123038 (US20110068086A1)
Patent Literature 2: JP-A-S59-46251
Patent Literature 3: JP-A-2009-292749
Patent Literature 4: U.S. Pat. No. 2,550,953

Non Patent Literature

Non Patent Literature 1: Bulletin of the Chemical Society of Japan, Vol. 41, 1724 (1968).

SUMMARY OF INVENTION

Technical Problem

As described above, several methods for producing 2-fluorobutane have hitherto been known.

However, in the method described in Patent Literature 2, the fluorinating agent used itself is extremely high in price, and in the method described in Patent Literature 3, an alkyl lithium involving a risk of ignition is used. The present inventor tried a reaction in the absence of a solvent, according to the description of Non Patent Literature 1, and have found that by-produced is a large amount of an acetic acid alkyl ester, a by-product, in which the methyl group portion of a methyl alkyl ether is substituted with an acetyl group derived from the fluorinating agent.

In this way, there has been a problem that it is difficult to apply the conventional methods for producing 2-fluorobutane from the viewpoint of the industrial productivity.

Under such circumstances as described above, in Japanese Patent Application No. 2014-24501, the present inventor has discovered that 2-fluorobutane is obtained in a good yield while the production of acetic acid alkyl esters, by-products, is being suppressed, when an alkyl ether compound of a secondary alcohol such as sec-butyl methyl ether or sec-butyl ethyl ether is used as a starting material, acetyl fluoride is used as a fluorinating agent, and an ether complex of boron trifluoride is used as a catalyst, in a hydrocarbon-based solvent.

However, a subsequent investigation has revealed that when 2-fluorobutane is brought into contact with a Lewis acid compound (boron trifluoride), 2-fluorobutane is partially decomposed into hydrogen fluoride and butenes, and thus it has been found that an improvement is necessary. It has also been found that when an ether complex of boron trifluoride is used, the ether compound constituting the complex is liberated in the reaction system, the liberated ether acts as an impurity for the fluorine compound as the target compound, and the liberated ether sometimes causes a load on the purification of the target compound, depending on the type of the liberated ether.

The present invention has been achieved under such circumstances as described above, and an object of the present invention is to provide a method for industrially advantageously producing 2-fluorobutane.

Solution to Problem

The present inventor made a diligent study to solve the above-described problem. Consequently, the present inventor has perfected the present invention by discovering that by using a catalyst in which boron trifluoride to be used as a catalyst is supported on a metal oxide, (a) an excessive contact between 2-fluorobutane produced by a reaction and boron trifluoride is avoided, and consequently the decomposition of 2-fluorobutane can be suppressed; (b) the production of the ether compounds (impurities) derived from the boron trifluoride-ether complex can also be suppressed; and (c) by recovering and reusing the metal oxide-supported boron trifluoride catalyst, the reduction of the amounts of waste substances and the simplification of the posttreatment after the reaction are achieved.

Thus, the present invention provides the following methods (i) to (v) for producing a fluorinated hydrocarbon represented by a structural formula (3).

(i) A method for producing a fluorinated hydrocarbon represented by the structural formula (3), wherein an ether compound represented by a structural formula (1) and an acid fluoride represented by a structural formula (2) are brought into contact with each other in a hydrocarbon-based solvent, in the presence of a catalyst in which boron trifluoride is supported on a metal oxide: Structural formula (1)

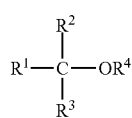
Structural formula (1)

wherein $R^1$ and $R^2$ each independently represent an alkyl group having 1 to 3 carbon atoms, $R^3$ represents a hydrogen atom, a methyl group or an ethyl group, and $R^4$ represents a methyl group or an ethyl group; and $R^1$ and $R^2$ may be bonded to each other to form a cyclic structure, Structural formula (2)

Structural formula (2)

wherein $R^5$ represents a methyl group or an ethyl group, Structural formula (3)

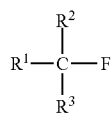
Structural formula (3)

wherein $R^1$ to $R^3$ represent the same meanings as described above.

(ii) The production method according to (i), wherein the metal oxide is at least one selected from aluminum oxide, titanium oxide and zirconium oxide.

(iii) The production method according to (i) or (ii), wherein the ether compound represented by the structural formula (1) is sec-butyl methyl ether or t-butyl methyl ether.

(iv) The production method according to any one of (i) to (iii), wherein the acid fluoride represented by the structural formula (2) is acetyl fluoride.

(v) The production method according to any one of (i) to (iv), wherein the fluorinated hydrocarbon represented by the structural formula (3) is 2-fluorobutane.

Advantageous Effects of Invention

According to the present invention, the target fluorinated hydrocarbon can be industrially advantageously produced. Specifically, according to the present invention, by using a catalyst in which boron trifluoride is supported on a metal oxide as a Lewis acid catalyst, (a) an excessive contact between 2-fluorobutane produced by a reaction and boron trifluoride is avoided, and consequently the decomposition of 2-fluorobutane can be suppressed; (b) the production of the ether compounds (impurities) derived from the boron trifluoride-ether complex can also be suppressed; and (c) by recovering and reusing the metal oxide-supported boron trifluoride catalyst, the reduction of the amounts of waste substances and the simplification of the posttreatment after the reaction can be achieved.

DESCRIPTION OF EMBODIMENTS

Hereinafter, the present invention is described in detail.

The present invention is a method for producing a fluorinated hydrocarbon represented by the structural formula (3) by bringing the ether compound represented by the structural formula (1) and the acid fluoride represented by the structural formula (2) into contact with each other in a hydrocarbon-based solvent, in the presence of a catalyst in which boron trifluoride is supported on a metal oxide (hereinafter, sometimes also referred to as "the metal oxide-supported boron trifluoride catalyst").

The starting material used in the present invention is the ether compound (hereinafter, sometimes also referred to as "the ether compound (1)") represented by the structural formula (1).

In the structural formula (1), $R^1$ and $R^2$ each independently represent an alkyl group having 1 to 3 carbon atoms. $R^3$ represents a hydrogen atom, a methyl group or an ethyl group, and $R^4$ represents a methyl group or an ethyl group.

The ether compound (1) is preferably an ether compound in which the total number of the carbon atoms in $R^1$ to $R^3$ is 3 or 4. Examples of the alkyl groups of $R^1$ and $R^2$ having 1 to 3 carbon atoms include a methyl group, an ethyl group, an n-propyl group and an isopropyl group.

$R^1$ and $R^2$ may also be bonded to each other to form a cyclic structure, but are preferably in a state of not forming a cyclic structure.

Examples of the cyclic structure formed by bonding of $R^1$ and $R^2$ to each other include a cyclopropane ring, a cyclobutane ring, a cyclopentane ring, a cyclohexane ring and a cycloheptane ring.

Specific examples of the ether compound (1) include: methyl ethers such as sec-butyl methyl ether, t-butyl methyl ether, cyclobutyl methyl ether, 2-pentyl methyl ether, 3-pentyl methyl ether, 2-methyl-2-butyl methyl ether and cyclopentyl methyl ether; and ethyl ethers such as sec-butyl ethyl ether, t-butyl ethyl ether, cyclobutyl ethyl ether, 2-pentyl ethyl ether, 3-pentyl ethyl ether, 2-methyl-2-butyl ethyl ether and cyclopentyl ethyl ether.

From easy availability of the raw materials, preferable among these are alkyl methyl ethers in which the alkyl group has 4 carbon atoms and alkyl ethyl ether in which the alkyl group has 4 carbon atoms such as sec-butyl methyl ether, t-butyl methyl ether, sec-butyl ethyl ether and t-butyl ethyl ether.

Examples of the method for producing the ether compound (1) include, without being particularly limited to: heretofore known methods such as a method described in Journal of Japan Oil Chemists' Society (Yukagaku), Vol. 31, p. 960 (1982), and a method described in Journal of American Chemical Society, Vol. 54, 2088 (1932). The former method is a method in which the corresponding alcohol is brought into contact with a sulfuric acid ester in the presence of a phase-transfer catalyst such as a 50% concentration of sodium hydroxide and tetraalkylammonium salt. The latter method is a method in which the corresponding anhydrous alcohol is brought into contact with metallic sodium, and then brought into contact with an alkyl bromide or an alkyl iodide to produce an ether compound.

The fluorinating agent used in the present reaction is the acid fluoride (hereinafter, sometimes also referred to as "the acid fluoride (2)") represented by the structural formula (2).

In the structural formula (2), $R^5$ is a methyl group or an ethyl group. The acid fluoride (2) is specifically acetyl fluoride or propionyl fluoride.

The acid fluoride (2) is a heretofore known substance, can be produced by a heretofore known method, and is available. The acid fluoride (2) can be produced according to the method described in, for example, Journal of Chemical Society Dalton Transaction, 2129 (1975), or Journal of American Chemical Society, Vol. 59, 1474 (1937). The former method is a method in which potassium fluoride is dissolved in acetic acid, acetyl chloride or propionyl chloride is added under heating, and generated acetyl fluoride or propionyl fluoride is collected. The latter method is a method in which sodium hydrogen difluoride is dissolved in anhydrous acetic acid, acetyl chloride is added, and the generated acetyl fluoride is collected.

The amount of the acid fluoride (2) used is preferably 0.8 to 1.3 equivalents and more preferably 0.9 to 1.2 equivalents in relation to the ether compound (1). When the amount of the acid fluoride (2) used falls within such a range, the productivity is excellent, and the posttreatment or the purification process is preferably not cumbersome.

Of the acid fluorides (2), acetyl fluoride is converted into methyl acetate when acetyl fluoride acts as a fluorinating agent, and then a methyl ether compound is used as the ether compound (1). Acetyl fluoride is converted into ethyl acetate when an ethyl ether compound is used. When propionyl fluoride is used, propionyl fluoride is similarly converted into methyl propionate or ethyl propionate respectively.

As the hydrocarbon-based solvent used in the present invention, in consideration of the load in the purification process (distillation purification), it is preferable to use a hydrocarbon-based solvent having a boiling point higher by 25° C. or more than the boiling point of the fluorinated hydrocarbon, the product.

Specific examples of such a hydrocarbon-based solvent include: hydrocarbon-based solvents having 5 carbon atoms such as n-pentane and cyclopentane; hydrocarbon-based solvents having 6 carbon atoms such as n-hexane, 2-methylpentane, 3-methylpentane, 2,2-dimethylbutane, 2,3-dimethylbutane, cyclohexane and methylcyclopentane; hydrocarbon-based solvents having 7 carbon atoms such as n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, methylcyclohexane, cycloheptane and toluene; hydrocarbon-based solvents having 8 carbon atoms such as n-octane, 4-methylheptane, 2-methylheptane, 3-methylheptane, 2,2-dimethylhexane, 2,3-dimethylhexane, 2,4-dimethylhexane, 2,5-dimethylhexane, 3,3-dimethylhexane, 3,4-dimethylhexane, 3-ethylhexane, 2,2,3-trimethylpentane, 2,2,4-trimethylpentane, 2,3,3-trimethylpentane, 2,3,4-trimethylpentane, 2-methyl-3-ethylpentane, 3-methyl-3-ethylpentane, cyclooctane, ethyl benzene and xylene. When the hydrocarbon-based solvents are mutually in a relationship of being isomers, a mixture of composed such isomers may also be used as a hydrocarbon-based solvent.

From the viewpoint of easiness in handling, more preferable among these are: hydrocarbon-based solvents having 6 carbon atoms such as n-hexane, 2-methylpentane, 3-methylpentane, 2,2-dimethylbutane, 2,3-dimethylbutane, cyclohexane and methylcyclopentane; and hydrocarbon-based solvents having 7 carbon atoms such as n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane, methylcyclohexane, cycloheptane and toluene.

The amount of each of these hydrocarbon-based solvents used is usually 1 to 10 ml, preferably 2 to 5 ml, and more preferably 2.5 to 3 ml, in relation to 1 g of the ether compound (1) to be a raw material. When the amount of the hydrocarbon-based solvent used is too small, the amount of the acetic acid alkyl ester produced as a by-product is increased, and when the amount of the hydrocarbon-based solvent used is too large, a long period of time is required until the reaction is completed, or the treatment of the waste liquid during posttreatment comes to be cumbersome.

In the present invention, as the catalyst, a metal oxide-supported boron trifluoride catalyst is used.

The metal oxide-supported boron trifluoride catalyst can be prepared according to, for example, the method described in Journal of Organic Chemistry, Vol. 61, 3496 (1996), or the method described in U.S. Pat. No. 4,407,731. The former method is a method in which a diethyl ether complex of boron trifluoride is brought into contact with dried neutral alumina in an n-hexane solvent, and the produced slurry is concentrated and dried. The latter method is a method in which boron trifluoride in a gaseous state is brought into contact with dried 7-alumina at a high temperature to prepare the metal oxide-supported boron trifluoride catalyst.

Specific examples of the boron trifluoride complex used in the preparation of the metal oxide-supported boron trifluoride catalyst include an acetic acid complex of boron trifluoride, an acetonitrile complex of boron trifluoride, an ethylamine complex of boron trifluoride, a methanol complex of boron trifluoride, a propanol complex of boron trifluoride, a dimethyl sulfide complex of boron trifluoride, a phosphoric acid complex of boron trifluoride, a dimethyl ether complex of boron trifluoride, a diethyl ether complex of boron trifluoride, a t-butyl methyl ether complex of boron trifluoride, a dibutyl ether complex of boron trifluoride and a tetrahydrofuran complex of boron trifluoride. Among these, preferable are the ether compound complexes such as the dimethyl ether complex, the diethyl ether complex, the t-butyl methyl ether complex, the dibutyl ether complex and the tetrahydrofuran complex, and from the viewpoint of easiness in handling, more preferable are the diethyl ether complex, the tetrahydrofuran complex and the methanol complex.

Examples of the metal oxide used for the preparation of the metal oxide-supported boron trifluoride catalyst include aluminum oxide, titanium oxide, zirconium oxide and magnesium oxide.

The form of the metal oxide-supported boron trifluoride catalyst is not particularly limited, and may be various forms such as a powder form and a spherical form. More preferable among these metal oxides is aluminum oxide from the viewpoint of the handleability during the preparation or reaction of the metal oxide-supported boron trifluoride catalyst, or the easy availability as formed articles.

As these metal oxides, preferable are metal oxides fired and sufficiently dried immediately before supporting boron trifluoride, from the viewpoint of obtaining the more excellent advantageous effects of the present invention.

The concentration of boron trifluoride supported by the metal oxide is preferably 0.5 mmol to 10 mmol per the unit weight (g) of the metal oxide. When the support concentration is too small, the amount of the metal oxide-supported boron trifluoride catalyst used during reaction is large, and the constitution of the reaction system is difficult. On the other hand, when the support concentration is too large, the supported catalyst is sensitive to the moisture in the air, the supported boron trifluoride tends to be partially deactivated, and it is necessary to pay attention to the handling of the supported catalyst.

The amount of the metal oxide-supported boron trifluoride catalyst used is usually 0.01 to 10 mol % and preferably, 0.1 to 5 mol % in relation to the ether compound (1) to be a raw material. When the amount of the catalyst used is too small, a remarkable decrease of the reaction rate is caused; when the amount of the catalyst used is too large, the proportion of the solid component of the catalyst is large in relation to the liquid component of the reaction mixture, and thus the following failures are liable to be caused: the stirring is made difficult, and the reaction proceeds quickly to cause bumping.

The temperature of the reaction between the ether compound (1) and the acid fluoride (2) is preferably within a range from −30° C. to +30° C. and more preferably within a range from −10° C. to +20° C. Such a temperature range is preferable because the reaction rate is appropriate, the productivity is excellent, and the loss of the produced fluorinated hydrocarbon due to volatilization can be suppressed.

The reaction time depends on the combination of the ether compound (1) to be a raw material, the acid fluoride (2) and the hydrocarbon-based solvent or on the reaction scale, but is usually 0.5 to 10 hours and preferably 1 to 7 hours. When the reaction time is too short, the reaction is not completed, thus the unreacted raw material or the acid fluoride functioning as the fluorinating agent remains in a large amount so as to make the posttreatment cumbersome. When the reaction time is too long, the possibility of the progress of the excessive reaction is enhanced, and the production amount of the acetic acid alkyl ester, a by-product, is increased.

Examples of an embodiment of the reaction include a method in which a metal oxide-supported boron trifluoride catalyst and a hydrocarbon-based solvent are placed in a reactor; the reactor is cooled to a predetermined temperature (−30° C. to 0° C.); then, while the resulting mixture is being stirred, the ether compound (1) to be a raw material, and subsequently, the acid fluoride (2) to be a fluorinating agent are added in the reactor; and subsequently, the stirring of the contents is continued while the contents are being maintained at a predetermined temperature (−30° C. to +30° C.)

After the completion of the reaction, it is possible to adopt a method in which the metal oxide-supported boron trifluoride catalyst is separated by using a filter from the contents of the reaction system, and thus only the liquid component is collected; or a method in which the reaction is beforehand performed in a reactor equipped with a filtration function, the metal oxide-supported boron trifluoride catalyst is filtered off after the completion of the reaction, and only the liquid component is collected.

The filtered-off metal oxide-supported boron trifluoride catalyst is preferably placed in an atmosphere of an inert gas such as dry nitrogen or argon, in order to maintain the catalytic activity thereof. The separated and recovered metal oxide-supported boron trifluoride catalyst maintains the catalytic activity, and accordingly can be used repeatedly. Specifically, the following operations can be repeated: the separated and recovered metal oxide-supported boron trifluoride catalyst is placed in the reactor, the hydrocarbon-based solvent is again placed in the reactor; the reactor is cooled to an optional temperature; then, while all the contents are being stirred, the ether compound (1) to be a raw material, and subsequently, the acid fluoride (2) to be a fluorinating agent are added in the reactor; and the reaction is performed while the resulting mixture is being stirred.

On the other hand, the separated liquid component is distilled as it is, and consequently the fluorinated hydrocarbon, the target product, can be isolated. When the purity of the fluorinated hydrocarbon is desired to be further enhanced, a rectification may be again performed.

In the manner as described above, the fluorinated hydrocarbon represented by the structural formula (3) can be obtained.

Specific examples of the fluorinated hydrocarbon represented by the structural formula (3) obtained by the production method of the present invention include: 2-fluorobutane, t-butyl fluoride, 2-fluoropentane, 3-fluoropentane, 2-methyl-2-fluorobutane, cyclobutyl fluoride, cyclopentyl fluoride and cyclohexyl fluoride.

Preferable among these are 2-fluorobutane and t-butyl fluoride from the viewpoint of the easy availability of the raw materials.

EXAMPLES

Hereinafter, by way of Examples, the present invention is described in further details, but the scope of the present invention is not limited by following Examples. Note that "%" represents "wt %" unless otherwise specified.

The analytical conditions adopted hereinafter are as follows.

Gas Chromatography Analysis (GC Analysis)
Apparatus: HP-6890 (manufactured by Agilent Technologies, Inc.)
Column: Inert Cap-1, manufactured by GL Sciences Inc., length: 60 m, inner diameter: 0.25 mm, film thickness: 1.5 μm
Column temperature: Maintained at 40° C. for 10 minutes, subsequently, increased at a rate of 20° C./min, and then maintained at 40° C. for 10 minutes
Injection temperature: 200° C.
Carrier gas: Nitrogen
Split ratio: 100/1
Detector: FID
Gas Chromatography Mass Analysis
GC section: HP-6890 (manufactured by Agilent Technologies, Inc.)
Column: Inert Cap-1, manufactured by GL Sciences Inc., length: 60 m, inner diameter: 0.25 mm, film thickness: 1.5 μm
Column temperature: Maintained at 40° C. for 10 minutes, subsequently, increased at a rate of 20° C./min, and then maintained at 240° C. for 10 minutes
MS section: 5973 NETWORK manufactured by Agilent Technologies, Inc.
Detector: EI-type (acceleration voltage: 70 eV)

Production Example 1: Production of Sec-Butyl Methyl Ether

In a 500 ml volume eggplant flask with a stirring bar placed therein, 360 ml of 2-butanol and 37.3 g of flaky potassium hydroxide (manufactured by Aldrich Corporation, purity: approximately 90%) were placed, and the resulting mixture was stirred for approximately 2.5 hours at 50° C. When potassium hydroxide was dissolved to produce a uniform solution, the heating was once ceased. To the resulting uniform solution, 84.4 g of iodomethane was added, and the resulting mixture was stirred at 50° C. for a little over 3 hours in a state of being equipped with a Dimroth condenser. The eggplant flask was cooled to room temperature (approximately 25° C.), the supernatant solution was analyzed by gas chromatography, and thus it was found that iodomethane was virtually consumed, and the supernatant solution contained a mixture composed of 2-methoxybutane, the target substance, and 2-butanol. The content in the eggplant flask was filtered to filter off potassium iodide. The filtered-off potassium iodide was dissolved in a small amount of water, the upper layer of an organic phase was separated, the separated organic phase was mixed with the foregoing filtrate, and thus a filtrate mixture was obtained.

The obtained filtrate mixture was placed in a distillation still, and distilled by using a KS-type rectifier (manufactured by TOKA SEIKI Co., Ltd., column length: 30 cm, column packing material: Helipack No. 1). The fraction of the column top temperature of 55 to 56° C. was collected, the water azeotropically boiled and distilled was separated by using a separating funnel, the obtained distillate was dried with the molecular sieves 4A, and thus 38 g of sec-butyl methyl ether was obtained (yield: 72%).

GC-MS (EI-MS): m/z 73, 59, 41, 29

Production Example 2: Production of Sec-Butyl Ethyl Ether

In a 500 ml volume eggplant flask with a stirring bar placed therein, 240 ml of 2-butanol and 24.8 g of flaky potassium hydroxide (manufactured by Aldrich Corporation, purity: approximately 90%) were placed, and the resulting mixture was stirred for 3 hours at 50° C. When potassium hydroxide was dissolved to produce a uniform solution, the heating was once ceased. To the resulting uniform solution, 43 g of ethyl bromide was added, and the mixture was stirred at 70° C. for a little over 4 hours in a state of being equipped with a Dimroth condenser. The reaction mixture was cooled to room temperature (approximately 25° C.; the same shall apply hereinafter), the supernatant solution was analyzed by gas chromatography, and thus it was found that ethyl bromide was virtually consumed, and the supernatant solution was a mixture composed of 2-ethoxybutane, the target substance, and 2-butanol. Potassium bromide was filtered off from the content in the eggplant flask, to obtain a filtrate. The filtered-off potassium bromide was dissolved in a small amount of water, the upper layer of an organic phase was separated, and the separated organic phase was mixed with the foregoing filtrate (a filtrate mixture).

The obtained filtrate mixture was placed in a distillation still, and distilled by using a KS-type rectifier (manufactured by TOKA SEIKI Co., Ltd., column length: 30 cm, column packing material: Helipack No. 1). The fraction of the column top temperature of 68 to 69° C. was collected, the water azeotropically boiled and distilled was separated by using a separating funnel, the obtained distillate was dried with the molecular sieves 4A, and thus 31 g of sec-butyl ethyl ether was obtained (yield: 51%).

GC-MS (EI-MS): m/z 87, 73, 59, 45

Production Example 3: Production of 2-Pentyl Methyl Ether

In a 500 ml volume eggplant flask equipped with a Dimroth condenser, a dropping funnel and a stirring bar, 300 ml of 2-pentanol and 30 g of potassium hydroxide (manufactured by Wako Pure Chemical Industries, Ltd., purity: approximately 85%) were placed, and the resulting mixture was stirred for approximately 2.5 hours at 50° C. When potassium hydroxide was dissolved to produce a uniform solution, 81 g of methyl p-toluenesulfonate was added from a dropping funnel to the uniform solution over approximately 1 hour, and the resulting mixture was stirred at 50° C. for a little over 3 hours. The reaction mixture was cooled to room temperature, and the content was transferred into a beaker; water was added to the beaker, and thus the produced potassium p-toluenesulfonate was dissolved. The solution in the beaker was transferred into a separating funnel, the aqueous layer was separated, and thus a liquid mixture composed of 2-pentyl methyl ether and 2-pentanol was obtained.

The obtained liquid mixture was placed in a distillation still, and distilled by using a KS-type rectifier (manufactured by TOKA SEIKI Co., Ltd., column length: 30 cm, column packing material: Helipack No. 1). The fraction of the column top temperature of 74 to 75° C. was collected, the water azeotropically boiled and distilled was separated by using a separating funnel, the obtained distillate was dried with the molecular sieves 4A, and thus 16 g of 2-pentyl methyl ether was obtained (yield: 37%).

GC-MS (EI-MS): m/z 87, 71, 59, 45

Production Example 4: Production of Acetyl Fluoride

In a 500 ml volume glass reactor equipped with a stirrer, a dropping funnel and a collection trap, 200 ml of anhydrous acetic acid and 46.9 g of potassium hydrogen difluoride were placed, and the resulting mixture was stirred while being heated to 40° C. To the mixture, 47 g of acetyl chloride was dropwise added from the dropping funnel over 40 minutes, and after the completion of the dropwise addition, the temperature of the reactor was increased by 10° C. every 15 minutes. The reactor was finally heated to 90° C., and then maintained at that temperature for 20 minutes, and subsequently the reaction was terminated. Meanwhile, acetyl fluoride distilled from the reactor was collected in a glass trap cooled with ice water. The crude product amount was 47.6 g (crude yield: 128%). Note that in the present reaction, acetyl fluoride is also produced from anhydrous acetic acid, and accordingly the yield exceeds 100%.

The obtained crude acetyl fluoride was subjected to a simple distillation, the fraction of the column top temperature of 20 to 24° C. was collected, and thus 42.4 g of acetyl fluoride was obtained (yield: 114%).

Production Example 5: Production of Propionyl Fluoride

In a 500 ml volume glass reactor equipped with a stirrer, a dropping funnel and a collection trap, 200 ml of anhydrous propionic acid and 46.8 g of potassium hydrogen difluoride were placed, and the resulting mixture was stirred while being heated to 90° C. To the mixture, 55.5 g of propionyl chloride was dropwise added from the dropping funnel over 1 hour, and after the completion of the dropwise addition, the mixture was further stirred for 15 minutes. Subsequently, the temperature of the reactor was increased by 10° C. every 15 minutes, and the reactor was heated to 110° C. The resulting mixture was stirred at 110° C. for 30 minutes, and then the reaction was terminated. Meanwhile, propionyl fluoride distilled from the reactor was collected in a glass trap cooled with ice water. The crude yield was 132%. Note that in the present reaction, propionyl fluoride is also produced from anhydrous propionic acid, and accordingly the yield exceeds 100%.

The obtained crude propionyl fluoride was subjected to a simple distillation, the fraction of the column top temperature of 42 to 43° C. was collected, and thus 46.8 g of propionyl fluoride was obtained (yield: 103%).

Catalyst Preparation Example 1

A spherical alumina (manufactured by DKSH Inc., catalyst grade D) was sieved, and an alumina having a diameter of 2.8 mm or less was taken out and fired in a gaseous flow of nitrogen at 300° C. for 9 hours.

In a 100 ml volume eggplant flask, 5 g of the fired spherical alumina and a stirring bar were placed, and the eggplant flask was equipped with a three-way cock and placed in a nitrogen atmosphere. In the flask, 25 ml of dry n-hexane was placed, and the stirring of the n-hexane was slowly started. In the flask, 2.84 g of a boron trifluoride diethyl ether complex was added by using a syringe, and the resulting mixture was stirred at room temperature for 3 hours. Subsequently, the stirring bar was taken out, n-hexane was distilled off by using a rotary evaporator, then the bath temperature was set at 50° C. to dry up the remainder after distillation further over 1 hour, and thus a dried boron trifluoride-alumina catalyst was obtained (supported concentration of boron trifluoride: 4 mmol/g).

Catalyst Preparation Example 2

A spherical alumina (manufactured by DKSH Inc., catalyst grade D) was sieved, an alumina having a diameter of 2.8 mm or less was taken out, and was fired in a gaseous flow of nitrogen at 300° C. for 9 hours.

In a 100 ml volume eggplant flask, 5 g of the fired spherical alumina and a stirring bar were placed, and the eggplant flask was equipped with a three-way cock and placed in a nitrogen atmosphere. In the flask, 25 ml of dry n-hexane was placed, and the stirring of the n-hexane was slowly started. In the flask, 1.42 g of a boron trifluoride diethyl ether complex was added by using a syringe, and the resulting mixture was stirred at room temperature for 3 hours. Subsequently, the stirring bar was taken out, n-hexane was distilled off by using a rotary evaporator, then the bath temperature was set at 50° C. to dry up the remainder after distillation further over 1 hour, and thus a dried boron trifluoride-alumina catalyst was obtained (supported concentration of boron trifluoride: 2 mmol/g).

Catalyst Preparation Example 3

A spherical alumina (manufactured by DKSH Inc., catalyst grade D) was sieved, an alumina having a diameter of 2.8 mm or less was taken out, and was fired in a gaseous flow of nitrogen at 300° C. for 9 hours.

In a 100 ml volume eggplant flask, 2.5 g of the fired spherical alumina and a stirring bar were placed, and the eggplant flask was equipped with a three-way cock and placed in a nitrogen atmosphere. In the flask, 25 ml of dry n-hexane was placed, and the stirring of the n-hexane was slowly started. In the flask, 2.84 g of a boron trifluoride diethyl ether complex was added by using a syringe, and the resulting mixture was stirred at room temperature for 3 hours. Subsequently, the stirring bar was taken out, n-hexane was distilled off by using a rotary evaporator, then the bath temperature was set at 50° C. to dry up the remainder after distillation further over 1 hour, and thus a dried boron trifluoride-alumina catalyst was obtained (supported concentration of boron trifluoride: 8 mmol/g).

Catalyst Preparation Example 4

A spherical activated alumina (manufactured by Kanto Chemical Co., Inc., for use in column chromatograph) was sieved, an alumina having a diameter of 2.8 mm or less was taken out, and was fired in a gaseous flow of nitrogen at 300° C. for 9 hours.

In a 100 ml volume eggplant flask, 5 g of the fired spherical activated alumina and a stirring bar were placed, and the eggplant flask was equipped with a three-way cock and placed in a nitrogen atmosphere. In the flask, 25 ml of dry n-hexane was placed, and the stirring of the n-hexane was slowly started. In the flask, 2.84 g of a boron trifluoride diethyl ether complex was added by using a syringe, and the resulting mixture was stirred at room temperature for 3 hours. Subsequently, the stirring bar was taken out, n-hexane was distilled off by using a rotary evaporator, then the bath temperature was set at 50° C. to dry up the remainder after distillation further over 1 hour, and thus a dried boron trifluoride-alumina catalyst was obtained (supported concentration of boron trifluoride: 4 mmol/g).

Catalyst Preparation Example 5

A spherical alumina (manufactured by DKSH Inc., catalyst grade D) was sieved, an alumina having a diameter of 2.8 mm or less was taken out, and was fired in a gaseous flow of nitrogen at 300° C. for 9 hours.

In a 100 ml volume eggplant flask, 5 g of the fired spherical alumina and a stirring bar were placed, and the eggplant flask was equipped with a three-way cock and placed in a nitrogen atmosphere. In the flask, 25 ml of dry n-hexane was placed, and the stirring of the n-hexane was slowly started. In the flask, 2.78 g of a boron trifluoride tetrahydrofuran complex was added by using a syringe, and the resulting mixture was stirred at room temperature for 3 hours. Subsequently, the stirring bar was taken out, n-hexane was distilled off by using a rotary evaporator, then the bath temperature was set at 50° C. to dry up the remainder after distillation further over 1 hour, and thus a dried boron trifluoride-alumina catalyst was obtained (supported concentration of boron trifluoride: 4 mmol/g).

Catalyst Preparation Example 6

A spherical alumina (manufactured by DKSH Inc., catalyst grade D) was sieved, an alumina having a diameter of 2.8 mm or less was taken out, and was fired in a gaseous flow of nitrogen at 300° C. for 9 hours.

In a 100 ml volume eggplant flask, 2 g of the fired spherical alumina and a stirring bar were placed, and the eggplant flask was equipped with a three-way cock and placed in a nitrogen atmosphere. In the flask, 15 ml of dry methanol was placed, and the stirring of the n-hexane was slowly started. In the flask, 5.70 g of a 14 wt % methanol solution of boron trifluoride methanol complex was added by using a syringe, and the resulting mixture was stirred at room temperature for 3 hours. Subsequently, the stirring bar was taken out, methanol was distilled off by using a rotary evaporator, then the bath temperature was set at 50° C. to dry up the remainder after distillation further over 1 hour, and thus a dried boron trifluoride-alumina catalyst was obtained (supported concentration of boron trifluoride: 4 mmol/g).

Catalyst Preparation Example 7

A spherical silica gel (CARiACT Q-15, manufactured by Fuji Silysia Chemical Ltd.) was sieved, a spherical silica gel having a diameter of 2.8 mm or less was taken out, and was fired in a gaseous flow of nitrogen at 300° C. for 9 hours.

In a 100 ml volume eggplant flask, 5 g of the fired spherical silica gel and a stirring bar were placed, and the eggplant flask was equipped with a three-way cock and placed in a nitrogen atmosphere. In the flask, 25 ml of dry n-hexane was placed, and the stirring of the n-hexane was slowly started. In the flask, 2.84 g of a boron trifluoride diethyl ether complex was added by using a syringe, and the resulting mixture was stirred at room temperature for 3 hours. Subsequently, the stirring bar was taken out, n-hexane was distilled off by using a rotary evaporator, then the bath temperature was set at 50° C. to dry up the remainder after distillation further over 1 hour. In the flask, a dried boron trifluoride-silica catalyst was obtained (supported concentration of boron trifluoride: 4 mmol/g).

Example 1

In a 50 ml volume glass reactor equipped with a stirring bar and a Dimroth condenser, 0.5 g of the boron trifluoride-alumina catalyst prepared in Catalyst Preparation Example 1 and 10 ml of dry n-hexane were placed, and the resulting mixture was cooled to 0° C. To the cooled mixture, 3.52 g of sec-butyl methyl ether synthesized in Production Example 1 and 2.98 g of acetyl fluoride synthesized in Production Example 4 were added, and the resulting mixture was stirred for 3.5 hours while the temperature was being still maintained at 0° C. After the completion of the reaction, the reaction mixture was analyzed by gas chromatography, and consequently it was found that sec-butyl methyl ether, a raw material, nearly disappeared, 2-fluorobutane, the target compound, was produced in 22.79 area %, and 1-butene, (E)-2-butene and (Z)-2-butene were produced in 0.17 area %, 6.19 area % and 2.26 area %, respectively. In addition, 2-acetoxybutane attributable to the acetoxylation of the raw material was produced only in 0.33 area %. Note that the rest was composed of n-hexane, the solvent, and methyl acetate.

Example 2

A reaction was performed in the same manner as in Example 1, except that 0.5 g of the catalyst prepared in Catalyst Preparation Example 1 was replaced with 0.5 g of the catalyst prepared in Catalyst Preparation Example 2, and the reaction time was set at 7 hours. After the completion of the reaction, the reaction mixture was analyzed by gas chromatography, and consequently it was found that sec-butyl methyl ether, a raw material, nearly disappeared, 2-fluorobutane, the target compound, was produced in 21.23 area %, and 1-butene, (E)-2-butene and (Z)-2-butene were produced in 0.19 area %, 6.86 area % and 2.50 area %, respectively. In addition, 2-acetoxybutane attributable to the acetoxylation of the raw material was produced only in 1.16 area %.

Example 3

A reaction was performed in the same manner as in Example 1, except that 0.5 g of the catalyst prepared in Catalyst Preparation Example 1 was replaced with 0.5 g of the catalyst prepared in Catalyst Preparation Example 3. After the completion of the reaction, the reaction mixture was analyzed by gas chromatography, and consequently it was found that sec-butyl methyl ether, a raw material, nearly disappeared, 2-fluorobutane, the target compound, was produced in 20.72 area %, 1-butene, (E)-2-butene and (Z)-2-butene were produced in 0.13 area %, 4.89 area % and 1.96 area %, respectively, and sec-butyl methyl ether, the raw material, remained in 3.84 area %. In addition, 2-acetoxybutane attributable to the acetoxylation of the raw material was produced only in 1.05 area %.

Example 4

A reaction was performed in the same manner as in Example 1, except that 0.5 g of the catalyst prepared in Catalyst Preparation Example 1 was replaced with 0.5 g of the catalyst prepared in Catalyst Preparation Example 4. After the completion of the reaction, the reaction mixture was analyzed by gas chromatography, and consequently it was found that sec-butyl methyl ether, a raw material, nearly disappeared, 2-fluorobutane, the target compound, was produced in 23.60 area %, and 1-butene, (E)-2-butene and (Z)-2-butene were produced in 0.15 area %, 4.32 area % and 1.76 area %, respectively. In addition, 2-acetoxybutane attributable to the acetoxylation of the raw material was produced only in 0.62 area %.

Example 5

A reaction was performed in the same manner as in Example 1, except that 2.98 g of acetyl fluoride synthesized in Production Example 4 was replaced with 3.65 g of propionyl fluoride synthesized in Production Example 5, and the reaction time was set at 5 hours. After the completion of the reaction, the reaction mixture was analyzed by gas chromatography, and consequently it was found that sec-butyl methyl ether, a raw material, nearly disappeared, 2-fluorobutane, the target compound, was produced in 17.96 area %, and 1-butene, (E)-2-butene and (Z)-2-butene were produced in 0.19 area %, 4.53 area % and 1.72 area %, respectively. In addition, 2-propionyloxybutane attributable to the propionyloxylation of the raw material was produced only in 1.11 area %.

Example 6

A reaction was performed in the same manner as in Example 1, except that 10 ml of n-hexane was replaced with 10 ml of cyclohexane. After the completion of the reaction, the reaction mixture was analyzed by gas chromatography, and consequently it was found that sec-butyl methyl ether, a raw material, nearly disappeared, 2-fluorobutane, the target compound, was produced in 19.71 area %, and 1-butene, (E)-2-butene and (Z)-2-butene were produced in 0.18 area %, 6.79 area % and 2.37 area %, respectively. In addition, 2-acetoxybutane attributable to the acetoxylation of the raw material was produced only in 0.58 area %.

Example 7

A reaction was performed in the same manner as in Example 1, except that 10 ml of n-hexane was replaced with 10 ml of n-heptane. After the completion of the reaction, the reaction mixture was analyzed by gas chromatography, and consequently it was found that sec-butyl methyl ether, a raw material, nearly disappeared, 2-fluorobutane, the target compound, was produced in 20.83 area %, and 1-butene, (E)-2-butene and (Z)-2-butene were produced in 0.18 area %, 6.09 area % and 2.31 area %, respectively. In addition, 2-acetoxybutane attributable to the acetoxylation of the raw material was produced only in 0.66 area %.

Example 8

A reaction was performed in the same manner as in Example 1, except that 3.52 g of sec-butyl methyl ether synthesized in Production Example 1 was replaced with 4.08 g of sec-butyl ethyl ether synthesized in Production Example 2. After the completion of the reaction, the reaction mixture was analyzed by gas chromatography, and consequently it was found that sec-butyl methyl ether, a raw material, nearly disappeared, 2-fluorobutane, the target compound, was produced in 22.12 area %, and 1-butene, (E)-2-butene and (Z)-2-butene were produced in 0.12 area %, 3.90 area % and 1.31 area %, respectively. In addition, 2-acetoxybutane attributable to the acetoxylation of the raw material was produced only in 1.81 area %.

Example 9

A reaction was performed in the same manner as in Example 1, except that 3.52 g of sec-butyl methyl ether synthesized in Production Example 1 was replaced with 4.08 g of 2-pentyl ethyl ether synthesized in Production Example 3, and the solvent was changed from n-hexane to n-heptane. After the completion of the reaction, the reaction mixture was analyzed by gas chromatography, and consequently it was found that sec-pentyl ethyl ether, a raw material, nearly disappeared, 2-fluoropentane, the target compound, was produced in 17.70 area %, 3-fluoropentane was produced in 5.44 area %, and a mixture of isomers of pentene was produced in 5.29 area %. In addition, 2-acetoxypentane attributable to the acetoxylation of the raw material was produced only in 0.72 area %.

Example 10

A reaction was performed in the same manner as in Example 1, except that 3.52 g of sec-butyl methyl ether synthesized in Production Example 1 was replaced with 3.52 g of t-butyl methyl ether (manufactured by Tokyo Chemical Industry Co., Ltd.). After the completion of the reaction, the reaction mixture was analyzed by gas chromatography, and consequently it was found that t-butyl methyl ether, a raw material, nearly disappeared, t-butyl fluoride, the target compound, was produced in 23.89 area %, and isobutene was produced in 2.22 area %. In addition, acetoxy t-butyl attributable to the acetoxylation of the raw material was produced only in 0.97 area %.

Example 11

A reaction was performed in the same manner as in Example 1, except that 3.52 g of sec-butyl methyl ether synthesized in Production Example 1 was replaced with 4.08 g of t-butyl ethyl ether (manufactured by Tokyo Chemical Industry Co., Ltd.). After the completion of the reaction, the reaction mixture was analyzed by gas chromatography, and consequently it was found that t-butyl ethyl ether, a raw material, nearly disappeared, t-butyl fluoride, the target compound, was produced in 22.90 area %, and isobutene was produced in 2.32 area %. In addition, acetoxy t-butyl attributable to the acetoxylation of the raw material was produced only in 0.79 area %.

Example 12

A reaction was performed in the same manner as in Example 1, except that 0.5 g of the catalyst prepared in Catalyst Preparation Example 1 was replaced with 0.5 g of the catalyst prepared in Catalyst Preparation Example 5. After the completion of the reaction, the reaction mixture was analyzed by gas chromatography, and consequently it was found that sec-butyl ethyl ether, a raw material, nearly disappeared, 2-fluorobutane, the target compound, was produced in 22.29 area %, and 1-butene, (E)-2-butene and (Z)-2-butene were produced in 0.16 area %, 4.71 area % and 2.08 area %, respectively. In addition, 2-acetoxybutane attributable to the acetoxylation of the raw material was produced only in 0.62 area %. From the above-described results, it has been found that the advantageous effects of the present invention are achieved even when used is the metal oxide-supported boron trifluoride catalyst prepared with the boron trifluoride complex different from the boron trifluoride complex in Catalyst Preparation Example 1.

Example 13

A reaction was performed in the same manner as in Example 1, except that 0.5 g of the catalyst prepared in Catalyst Preparation Example 1 was replaced with 0.5 g of the catalyst prepared in Catalyst Preparation Example 6. After the completion of the reaction, the reaction mixture was analyzed by gas chromatography, and consequently it was found that sec-butyl ethyl ether, a raw material, nearly disappeared, 2-fluorobutane, the target compound, was produced in 22.76 area %, and 1-butene, (E)-2-butene and (Z)-2-butene were produced in 0.18 area %, 4.56 area % and 1.08 area %, respectively. In addition, 2-acetoxybutane attributable to the acetoxylation of the raw material was produced only in 0.66 area %. From the above-described results, it has been found that the advantageous effects of the present invention are achieved even when used is the metal oxide-supported boron trifluoride catalyst prepared with a solvent different from the solvent in Catalyst Preparation Example 1.

Example 14

In a 100 ml volume stainless steel autoclave, having a filter attached thereto, equipped with a valve and a stirrer, 1.5 g of the catalyst prepared in Catalyst Preparation Example 1 was filled, and the inside of the reaction system was reduced in pressure, and then made to be under a nitrogen atmosphere. In the autoclave, 30 ml of dry n-hexane was placed, and the autoclave was cooled to 0° C. From the valve, through a syringe, 10.6 g of 2-butyl methyl ether, and then 9.0 g of acetyl fluoride were placed in the autoclave, and the resulting mixture was stirred at 0 to 15° C. for 4 hours. Then, the stirring was ceased, the bottom valve of the autoclave was opened, and the reaction solution was extracted while being slightly pressurized with dry nitrogen. The reaction solution was colorless and transparent and was analyzed by gas chromatography, and consequently it was found that sec-butyl methyl ether, a raw material, nearly disappeared, 2-fluorobutane, the target compound, was produced in 22.53 area %, and 1-butene, (E)-2-butene and (Z)-2-butene were produced in 0.17 area %, 4.96 area % and 1.27 area %, respectively. In addition, 2-acetoxybutane attributable to the acetoxylation of the raw material was produced only in 0.57 area %.

In the autoclave in which the catalyst remained, 30 ml of dry n-hexane was again placed, and the autoclave was cooled to 0° C. From the valve, through a syringe, 10.6 g of sec-butyl methyl ether, and then 9.0 g of acetyl fluoride were placed in the autoclave, and the resulting mixture was stirred at 0 to 15° C. for 4 hours. Then, the stirring was ceased, the bottom valve of the autoclave was opened, and the reaction solution was extracted while being slightly pressurized with dry nitrogen. The reaction solution was colorless and transparent and was analyzed by gas chromatography, and consequently it was found that sec-butyl methyl ether, a raw material, nearly disappeared, 2-fluorobutane, the target compound, was produced in 22.23 area %, and 1-butene, (E)-2-butene and (Z)-2-butene were produced in 0.17 area %, 4.29 area % and 1.36 area %, respectively. In addition, 2-acetoxybutane attributable to the acetoxylation of the raw material was produced only in 0.89 area %.

This operation was repeated once more, the reaction solution was analyzed by gas chromatography, and consequently it was found that sec-butyl methyl ether, a raw material, nearly disappeared, 2-fluorobutane, the target compound, was produced in 22.02 area %, 1-butene, (E)-2-butene and (Z)-2-butene were produced in 0.14 area %, 4.71 area % and 1.55 area %, respectively, and 2-butyl methyl ether, a raw material, remained in 3.84 area %. In addition, 2-acetoxybutane attributable to the acetoxylation of the raw material was produced only in 0.79 area %.

From the above-described results, it has been found that the boron trifluoride-alumina catalyst prepared in Catalyst Preparation Example 1 can be used repeatedly, by filtering out the boron trifluoride-alumina catalyst from the reaction solution.

Comparative Example 1

A reaction was performed in the same manner as in Example 1, except that 0.5 g of the catalyst prepared in Catalyst Preparation Example 1 was replaced with 0.5 g of the catalyst prepared in Catalyst Preparation Example 7. After the completion of the reaction, the reaction mixture was analyzed by gas chromatography, and consequently it was found that 2-fluorobutane, the target compound, was produced in 14.79 area %, 1-butene, (E)-2-butene and (Z)-2-butene were produced in 0.13 area %, 4.89 area % and 1.94 area %, respectively, and sec-butyl ethyl ether, a raw material, remained in 5.93 area %. In addition, 2-acetoxybutane attributable to the acetoxylation of the raw material was produced in 2.05 area %.

In addition, it has been found that the boron trifluoride-silica gel catalyst is dissolved, and this catalyst cannot be recovered and reused.

Comparative Example 2

A reaction was performed in the same manner as in Example 1, except that n-hexane, the solvent, was not added. After the completion of the reaction, 10 ml of n-hexane was added in the reactor, and the resulting mixture was analyzed by gas chromatography, and consequently it was found that 2-fluorobutane, the target compound, was produced in 14.19 area %, 1-butene, (E)-2-butene and (Z)-2-butene were produced in 0.38 area %, 14.35 area % and 4.75 area %, respectively, and sec-butyl ethyl ether, a raw material, remained in 8.33 area %. In addition, 2-acetoxybutane attributable to the acetoxylation of the raw material was produced in 9.24 area %.

From this result, it has been found that when the reaction was performed without using any solvent, the production amounts of butene and 2-acetoxybutane, a by-product, are large.

Comparative Example 3

A reaction was performed in the same manner as in Example 1, except that the solvent was changed from n-hexane to methyl ethyl ketone. After the completion of the reaction, the reaction mixture was analyzed by gas chromatography, and consequently it was found that sec-butyl methyl ether, a raw material, remained in 11.93 area %, 2-flurobutane, the target compound, was produced in 6.79 area %, and several high boiling point species having unknown structures were produced in 6.56 area % in total.

Comparative Example 4

A reaction was performed in the same manner as in Example 1, except that the solvent was changed from n-hexane to ethyl acetate. After the completion of the reaction, the reaction mixture was analyzed by gas chromatography, and consequently it was found that sec-butyl methyl ether, a raw material, nearly disappeared, 2-fluorobutane, the target compound, was produced in 15.63 area %, and 1-butene, (E)-2-butene and (Z)-2-butene were produced in 0.29 area %, 12.56 area % and 3.54 area %, respectively. In addition, 2-acetoxybutane attributable to the acetoxylation of the raw material was produced in 0.37 area %. It has been found that as compared with Example 1, when ethyl acetate is used as the solvent, the production amounts of the butenes are large.

The invention claimed is:

1. A method for producing a fluorinated hydrocarbon represented by a structural formula (3), wherein an ether compound represented by a structural formula (1) and an acid fluoride represented by a structural formula (2) are brought into contact with each other in a hydrocarbon-based solvent, in the presence of a catalyst in which boron trifluoride is supported on a metal oxide:

Structural formula (1)

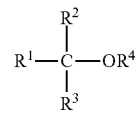

Structural formula (1)

wherein $R^1$ and $R^2$ each independently represent an alkyl group having 1 to 3 carbon atoms, $R^3$ represents a hydrogen atom, a methyl group or an ethyl group, and $R^4$ represents a methyl group or an ethyl group; and $R^1$ and $R^2$ may be bonded to each other to form a cyclic structure, Structural formula (2)

Structural formula (2)

wherein $R^5$ represents a methyl group or an ethyl group,

Structural formula (3)

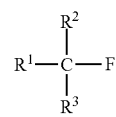

Structural formula (3)

wherein $R^1$ to $R^3$ represent the same meanings as described above.

2. The production method according to claim 1, wherein the metal oxide is at least one selected from aluminum oxide, titanium oxide and zirconium oxide.

3. The production method according to claim 1, wherein the ether compound represented by the structural formula (1) is sec-butyl methyl ether or t-butyl methyl ether.

4. The production method according to claim 1, wherein the acid fluoride represented by the structural formula (2) is acetyl fluoride.

5. The production method according to claim 1, wherein the fluorinated hydrocarbon represented by the structural formula (3) is 2-fluorobutane.

* * * * *